(12) United States Patent
Khan et al.

(10) Patent No.: US 9,561,184 B2
(45) Date of Patent: Feb. 7, 2017

(54) METHODS AND SYSTEMS FOR MULTI-STAGE DRYING OF PLASMA

(71) Applicant: Velico Medical, Inc., Beverly, MA (US)

(72) Inventors: Abdul Wahid Khan, Murrysville, PA (US); Michael Wilt, Windham, NH (US); Rud Karly Lucien, Lynn, MA (US); Jihae Sohn, Brighton, MA (US); Qiyong Peter Liu, Newton, MA (US)

(73) Assignee: Velico Medical, Inc., Beverly, MA (US)

( * ) Notice: Subject to any disclaimer, the term of this patent is extended or adjusted under 35 U.S.C. 154(b) by 0 days.

(21) Appl. No.: 14/670,127

(22) Filed: Mar. 26, 2015

(65) Prior Publication Data

US 2016/0082043 A1    Mar. 24, 2016

Related U.S. Application Data

(60) Provisional application No. 62/052,689, filed on Sep. 19, 2014.

(51) Int. Cl.
| | |
|---|---|
| *A61J 1/10* | (2006.01) |
| *F26B 3/06* | (2006.01) |
| *A61K 9/16* | (2006.01) |
| *F26B 5/04* | (2006.01) |
| *F26B 3/12* | (2006.01) |

(Continued)

(52) U.S. Cl.
CPC ............... *A61K 9/16* (2013.01); *A61K 9/1682* (2013.01); *A61K 9/1688* (2013.01); *F26B 3/06* (2013.01); *F26B 3/12* (2013.01); *F26B 5/04* (2013.01); *B65D 51/30* (2013.01); *B65D 81/266* (2013.01); *F26B 5/065* (2013.01)

(58) Field of Classification Search
CPC ............... F26B 5/06; F26B 5/065; F26B 3/10; F26B 3/12; F26B 3/00; F26B 3/14; F26B 3/32; F26B 5/00; F26B 5/04; F26B 5/041; F26B 5/042; F26B 5/044; F26B 17/10; F26B 17/12; F26B 21/006; F26B 21/02; F26B 21/14; F26B 25/008; F26B 5/045; F26B 5/16; B01D 1/16; B01D 1/18; B01D 1/20; B01D 9/0027; A61J 1/10; A61J 1/12; A61J 1/05; A61M 1/0209; A61M 1/0213; A61M 1/0231; B65D 81/266; B65D 51/244; B65D 51/30; B65D 81/267; B65D 81/268

See application file for complete search history.

(56) References Cited

U.S. PATENT DOCUMENTS 4,861,632 A * 8/1989 Caggiano .................. B32B 7/02
                                                            206/204
5,267,646 A * 12/1993 Inoue ..................... A61J 1/2093
                                                            206/204

(Continued)

FOREIGN PATENT DOCUMENTS

WO    2005079755 A2    9/2005

OTHER PUBLICATIONS

Carpenter, et al. "Rational Design of Stable Lyophilized Protein Formulations: Theory and Practice" Pharm Biotechnol; 2002; vol. 13; pp. 109-133.

(Continued)

*Primary Examiner* — Adam Marcetich
(74) *Attorney, Agent, or Firm* — Pierce Atwood LLP; Kevin M. Farrell; David J. Wilson

(57) ABSTRACT

Disclosed are methods of spray drying blood plasma using a two-step drying process.

20 Claims, 10 Drawing Sheets

(51) Int. Cl.
*F26B 5/06* (2006.01)
*B65D 81/26* (2006.01)
*B65D 51/30* (2006.01)

(56) References Cited

U.S. PATENT DOCUMENTS

| | | | | |
|---|---|---|---|---|
| 5,610,170 | A * | 3/1997 | Inoue | A61J 1/00 514/340 |
| 6,284,282 | B1 * | 9/2001 | Maa | A61K 9/0075 424/45 |
| 6,299,906 | B1 * | 10/2001 | Bausch | A61K 9/14 424/489 |
| 6,308,826 | B1 * | 10/2001 | Merrell | B65D 77/04 206/204 |
| 7,297,716 | B2 | 11/2007 | Shanbrom | |
| 8,518,452 | B2 | 8/2013 | Bjornstrup et al. | |
| 8,533,972 | B2 | 9/2013 | Hubbard, Jr. et al. | |
| 8,601,712 | B2 | 12/2013 | Hubbard, Jr. et al. | |
| 2003/0186004 | A1 * | 10/2003 | Koslow | B01J 20/28026 428/34.4 |
| 2005/0186183 | A1 * | 8/2005 | DeAngelo | A01N 1/02 424/93.7 |
| 2008/0119818 | A1 * | 5/2008 | Bakaltcheva | A01N 1/02 604/403 |
| 2008/0317640 | A1 * | 12/2008 | Mayer | A01N 37/16 422/400 |
| 2009/0145783 | A1 * | 6/2009 | Forker | B65D 81/266 206/204 |
| 2012/0103536 | A1 * | 5/2012 | Hubbard, Jr. | B01D 1/18 159/4.01 |
| 2014/0083627 | A1 | 3/2014 | Khan et al. | |
| 2014/0083628 | A1 | 3/2014 | Khan et al. | |
| 2014/0088768 | A1 | 3/2014 | Haley et al. | |
| 2014/0230266 | A1 * | 8/2014 | Luy | F26B 5/06 34/284 |

OTHER PUBLICATIONS

Lea, et al. "The Reaction Between Proteins and Reducing Sugars in the "Dry" State" Biochemistry and Biophysics; University of Cambridge; Jun. 5, 1950; vol. 5; Issue 3/4; pp. 433-454;—Article discloses the freeze drying of plasma and subsequent direct exposure to phosphorus pentoxide for further drying of the plasma. In contrast, the present invention teaches spray drying plasma and the indirect exposure of desiccant isolated from the plasma by a filter medium.

Schmid "Spray Drying of Protein Precipitates and Evaluation of the Nano Spray Dryer B-90" Dissertation, Ludwig Maximilian University of Munich; Jan. 3, 2011.

Shuja, et al. "Development and Testing of Low-Volume Hyperoncotic, Hyperosmotic Spray-Dried Plasma for the Treatment of Trauma-Associated Coagulopathy" J Trauma; May 2010; vol. 68; Issue 5; pp. 1084-1098.

* cited by examiner

METHODS AND SYSTEMS FOR MULTI-STAGE DRYING OF PLASMA

RELATED APPLICATION

This non-provisional application claims the benefit of priority in, and incorporates by reference the entire contents of, U.S. provisional application No. 62/052,689, filed Sep. 19, 2014, and entitled "Spray Drier Assemblies and Methods for Automated Spray Drying."

GOVERNMENT SUPPORT

The inventions described in this disclosure were made with Government support under contract HHSO100201200005C awarded by the Biomedical Advanced Research and Development Authority (BARDA). The Government may have certain rights in the inventions.

TECHNICAL FIELD

The present disclosure relates generally to preparing spray dried powders and in particular to two stage drying of blood plasma by controlled desiccation through a membrane such as a wall of a human blood plasma collection bag and de-oxygenation by oxygen scavenging through a membrane such as a wall of a human blood plasma collection bag. The inventions have numerous other applications as well.

BACKGROUND

Making up about 55% of the total volume of whole blood, blood plasma is a whole blood component in which blood cells and other constituents of whole blood are suspended. Blood plasma further contains a mixture of over 700 proteins and additional substances that perform functions necessary for bodily health, including clotting, protein storage, and electrolytic balance, amongst others. When extracted from whole blood, blood plasma may be employed to replace bodily fluids, antibodies, and clotting factors. Accordingly, blood plasma is extensively used in medical treatments.

To facilitate storage and transportation of blood plasma until use, plasma is typically preserved by freezing soon after its collection from a donor. Fresh-Frozen Plasma (FFP) is obtained through a series of steps involving centrifugation of whole blood to separate plasma and then freezing the collected plasma within less than 8 hours of collecting the whole blood. In the United States, the American Association of Blood Banks (AABB) standard for storing FFP is storage up to 12 months from collection when stored at temperature of −18° C. or below. FFP may also be stored for up to 7 years from collection if maintained at a temperature of −65° C. or below. In Europe, FFP has a shelf life of only 3 months if stored at temperatures between −18° C. to −25° C., and for up to 36 months if stored at colder than −25° C. If thawed, European standards dictate that the plasma must be transfused immediately or stored at 1° C. to 6° C. and transfused within 24 hours. If stored longer than 24 hours, the plasma must be relabeled for other uses or discarded.

Notably, however, FFP must be kept in a temperature-controlled environment of −18° C. or colder throughout its duration of storage to prevent degradation of certain plasma proteins and maintain its efficacy, which adds to the cost and difficulty of storage and transport. Furthermore, FFP must be thawed prior to use, resulting in a delay of 30-80 minutes before it may be used after removal from cold storage.

Accordingly, there is a need to develop alternative techniques for recovery and storage of plasma.

SUMMARY

The following patents and applications are incorporated herein by reference. U.S. non-provisional application Ser. No. 13/952,541, filed Jul. 26, 2013, and entitled "Automated Spray Drier;" which claims priority in U.S. provisional application No. 61/856,954, filed on Jul. 22, 2013, U.S. provisional application No. 61/820,428, filed on May 7, 2013, and U.S. provisional application No. 61/706,759, filed on Sep. 27, 2012; U.S. non-provisional application Ser. No. 13/953,458, filed Jul. 29, 2013, and entitled "Automated Spray Drier Control System," which claims priority in U.S. provisional application No. 61/706,759, filed on Sep. 27, 2012, U.S. provisional application No. 61/820,428, filed on May 7, 2013, and U.S. provisional application No. 61/856,954, filed on Jul. 22, 2013; and U.S. non-provisional application Ser. No. 13/953,198, filed Jul. 29, 2013, and entitled "Spray Drier Assembly for Automated Spray Drying," which claims priority to U.S. provisional application No. 61/706,759, filed on Sep. 27, 2012, U.S. provisional application No. 61/820,428, filed on May 7, 2013, and U.S. provisional application No. 61/856,957, filed on Jul. 22, 2013; U.S. Pat. No. 8,601,712, filed Oct. 25, 2012, entitled "System and Method for Spray Drying a Liquid," U.S. Pat. No. 8,533,972, filed Oct. 25, 2012, U.S. Pat. No. 8,595,950, filed May 17, 2012, all of which are divisions of application Ser. No. 13/284,320, now U.S. Pat. No. 8,533,971, filed Oct. 29, 2011, which cites priority to provisional application No. 61/408,438, filed Oct. 29, 2010.

A long-standing need and challenge to the blood industry has been to provide safe, reliable and convenient blood products while recovering in processing and preserving the efficacy and safety of the active components of those products in storage (stability) such as human blood plasma proteins known as clotting and coagulation factors ("factors") and when used in transfusion or as a source a medical treatments. The present disclosure provides efficacy preservation in storage and includes the recovery and stability of the clotting factors in the plasma in a manner that does not otherwise harm the plasma or the transfused patient. During spray drying, some blood plasma clotting factors may degrade to some extent, due to exposure to shear and other forces or other environmental stresses. Clotting factors may be subject to shearing stresses depending on the spray drying conditions. The methods and compositions of the present disclosure recognize that the denaturing effects of shear stress can be reduced or decreased by an enhanced multi-stage drying method using controlled desiccation of the dried plasma and its local environment through a relatively water vapor permeable membrane such as an external wall of a collection bag containing the dried plasma while the desiccant and the collection bag are both separately placed in a storage container such as a relatively water vapor impermeable aluminum sealed outer envelope or pouch. Moreover stability of the dried plasma may be enhanced by de-oxygenation of the dried plasma and its local environment by an oxygen scavenger through a relatively oxygen permeable membrane such as an exterior wall of a collection bag containing the dried plasma while the collection bag and the oxygen scavenger are both separately placed in a storage container such as a relatively oxygen impermeable aluminum sealed outer envelope or pouch. As discussed further below, the invention described herein has numerous applications other than moisture control and de-oxygenation of spray dried human blood plasma. For example, the present inventions may be used to efficaciously control moisture or oxygen content on lyophilized blood plasma stored in a relatively water vapor or oxygen permeable container such as a plastic bag or bottle.

There are many blood plasma factors associated with clotting. The methods and compositions of the present disclosure include recovering amounts of active/undenatured FGN, F V, F VII, F IX and vWF from rehydrated plasma that has undergone the spray drying process. vWF, also known as von Willibrand factor, has generally been difficult to recover and has become one indicator for recovery of all factors. In an embodiment, if vWF is recovered, the other factors are likely to be recovered as well. The inventors have discovered that three parameters are consequential to both recovery of human blood plasma factors and their long-term stability (preservation) in storage. These are: 1) the amount of heat that the plasma proteins are exposed to during the drying process is related to the amount recoverable functional plasma protein. Generally, the lower the heat temperature and time of exposure to heat the greater amount of functional protein is recovered. 2) The moisture content during storage in the local storage environment is related to stability (preservation) of the plasma protein during storage of the plasma protein. Generally, the lower the moisture content the greater the stability (preservation) of the plasma protein during storage. 3) The amount of oxidation to which the stored material such a spray dried plasma proteins is exposed in storage is related to stability (preservation) of the plasma proteins in storage. Generally, the less the oxidation in the local storage environment the greater the stability (preservation) of the material such as plasma proteins in storage.

The inventors have discovered novel ways to control and optimize these critical parameters by developing a two-stage drying process wherein the first drying stage utilizes a controlled spray drying process and the second drying stage uses desiccant in a closed environment. Oxidation is controlled through the use of oxygen scavenger(s) in a closed environment.

In this regard, the present invention contemplates a method for spray drying blood plasma, the method comprising: providing a spray drier device having a collection bag; providing blood plasma; spray drying the blood plasma using the spray drier device to produce a dried plasma product recovered in a vapor permeable collection bag, the dried plasma product having a moisture content at a first moisture level, the first moisture level being associated with a substantially non-clumping dried plasma; removing the collection bag from the spray drier device and sealing the collection bag; incubating the sealed collection bag containing dried plasma product in vapor communication with a desiccant material located outside the collection bag having sufficient capacity to lower the moisture content of the dried plasma product from the first moisture level to a second moisture level.

The present invention further contemplates that plasma factor activity in the dried plasma product is preserved to a greater extent through storage at the second moisture level relative to storage at the first moisture level.

The present invention further contemplates that the first moisture level is from about 3.5% to about 9.5%. The present invention further contemplates that the second moisture level is from about 1.5% to about 6.0%. The present invention further contemplates that the desiccant material has a mass that is determined as a function of a mass of the dried plasma product, the first moisture level, and the second moisture level. The present invention further contemplates that the desiccant material has a mass that is determined as a function of storage temperature.

The present invention further contemplates that incubating the dried plasma product further comprises storing both the collection bag and the desiccant material within a sealed, substantially vapor impermeable storage pouch. The present invention further contemplates storing an oxygen scavenger material outside of the collection bag, wherein the dried plasma maintains vapor communication with the oxygen scavenger material through the collection bag. The present invention further contemplates that the collection bag is sealed prior to being removed from the spray drier device.

The present invention contemplates a method for storing dried plasma product, the method comprising: providing a spray dryer, a vapor-permeable collection bag, a vapor impermeable storage pouch, desiccant and blood plasma; drying the blood plasma in the spray dryer to produce a dried plasma product containing preserved blood plasma clotting factors, the dried plasma product having a moisture content at a first moisture level, wherein the first moisture level is associated with a substantially non-clumping dried plasma product; and collecting the dried plasma product in the vapor permeable collection bag; placing the collection bag containing the dried plasma product in the vapor non-permeable storage pouch containing the desiccant wherein the desiccant is located in the storage pouch outside the collection bag and wherein the desiccant is selected at an amount sufficient to absorb moisture from the dried plasma through the collection bag and to lower the moisture content of the dried plasma product to a desired second moisture level and wherein the desired second moisture level is selected for a combination of stability and preservation of the clotting factors.

The present invention further contemplates that the collection bag comprises: an internal filter bag for containing the dried plasma product and an external bag for containing the filter bag, wherein both the filter bag and the external bag are vapor permeable.

The present invention further contemplates that the external bag comprises polyvinyl chloride (PVC). The present invention further contemplates that the filter bag comprises 0.2 micron filter material.

The present invention further contemplates that the first moisture level is from about 3.5% to about 9.5%. The present invention further contemplates that the second moisture level is from about 1.5% to about 6.0%. The present invention further contemplates that the desiccant material has a mass that is a function of a mass of the dried plasma product, the first moisture level, and the second moisture level. The present invention further contemplates that the desiccant material has a mass that is a function of storage temperature.

The present invention further contemplates that drying blood plasma to a first moisture level is performed by a spray drier device.

The present invention contemplates a kit for incubating a dried plasma product, the kit comprising: a vapor permeable collection bag for collecting the dried plasma product; a desiccant material aliquot for removing moisture from the spray dried plasma product; and a vapor impermeable storage pouch for storing the vapor permeable collection bag and the desiccant material aliquot during processing and storage.

The present invention further contemplates a plasma administration kit, the kit comprising: a vapor permeable collection container containing dried plasma product; a desiccant material for removing moisture from the spray dried plasma product; and a vapor impermeable storage pouch for storing the vapor permeable collection container and the desiccant material during storage. The present invention further contemplates that kit additionally comprises an oxygen scavenging material stored within the vapor impermeable storage pouch. The present invention further contemplates that the dried plasma product has a moisture level of about 1.5% to about 6.0%.

BRIEF DESCRIPTION OF THE DRAWINGS

The drawings are not necessarily to scale or exhaustive. Instead, emphasis is generally placed upon illustrating the principles of the embodiments described herein. The accompanying drawings, which are incorporated in this specification and constitute a part of it, illustrate several embodiments consistent with the disclosure. Together with the description, the drawings serve to explain the principles of the disclosure.

In the drawings.

DETAILED DESCRIPTION

Figure 1:
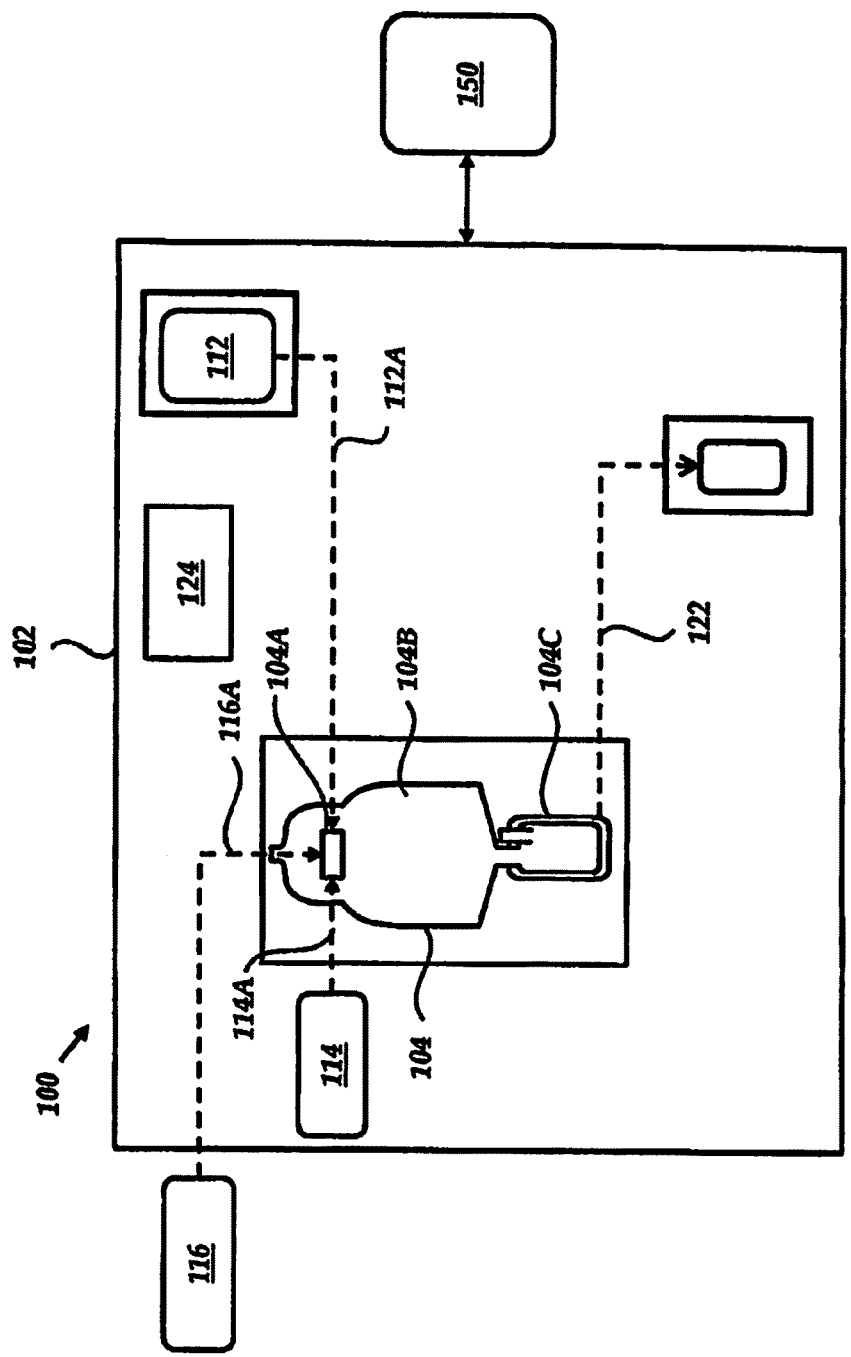
FIG. 1 is a schematic illustration of a spray drier system according to some embodiments.

The following detailed description refers to the accompanying drawings. The same or similar reference numbers may be used in the drawings or in the description to refer to the same or similar parts. Also, similarly named elements may perform similar functions and may be similarly designed, unless specified otherwise. Details are set forth to provide an understanding of the exemplary embodiments. Embodiments, e.g., alternative embodiments, may be practiced without some of these details. In other instances, well known techniques, procedures, and components have not been described in detail to avoid obscuring the described embodiments.

Embodiments of the present disclosure are directed to systems and methods for spray drying a liquid sample. In some embodiments, the liquid sample is plasma obtained from a blood donor. The disclosed embodiments, however, may be employed to spray dry other mixtures of solid particles in a continuous liquid medium, including, but not limited to, colloids, suspensions, and sols.

In general, a spray drier system is provided for spray drying a liquid sample such as blood plasma. In an embodiment, the spray drier system of the present disclosure includes a spray drier device and a spray drier assembly. The spray drier device is adapted, in an aspect, to receive flows of an aerosolizing gas, a drying gas, and plasma liquid sample from respective sources, and to couple with the spray drier assembly. The aerosolizing gas may be any suitable gas or gas mixture including filtered air or nitrogen. The drying gas may be any suitable gas or gas mixture including filtered and/or heated air or nitrogen. One or both gases may be moisture reduced by being passed through a drier or desiccant prior to use in the spray drier assembly of the present invention. The spray drier device may further transmit the received aerosolizing gas, drying gas, and plasma to the spray drier assembly. Spray drying of the plasma is performed in the spray drier assembly under the control of the spray drier device.

In some embodiments, the spray drier assembly includes a sterile, hermetically sealed enclosure body and a frame to which the enclosure body is attached. The frame defines first, second, and third portions of the assembly, separated by respective transition zones. A drying gas inlet is provided within the first portion of the assembly, adjacent to a first end of the enclosure body.

A spray drying head is further attached to the frame within the transition zone between the first and second portions of the assembly. This position also lies within the incipient flow path of the drying gas within the assembly. During spray drying, the spray drying head receives flows of an aerosolizing gas and plasma and aerosolizes the plasma with the aerosolizing gas to form aerosolized plasma (e.g., a suspension of liquid droplets in the gas). Drying gas additionally passes through the spray drying head to mix with the aerosolized plasma within the second portion of the assembly for drying. In the second portion of the assembly, which functions as a drying chamber, contact between the aerosolized plasma and the drying gas causes moisture to move from the aerosolized plasma to the drying gas, producing dried plasma and humid drying gas.

The spray drying head in an embodiment is adapted to direct the flow of drying gas within the drying chamber. For example, the spray drying head includes openings separated by fins which receive the flow of drying gas from the drying gas inlet. The orientation of the fins allows the drying gas to be directed in selected flow pathways (e.g., helical). Beneficially, by controlling the flow pathway of the drying gas, the path length over which the drying gas and aerosolized blood plasma are in contact within the drying chamber is increased, reducing the time to dry the plasma.

The dried plasma and humid drying gas subsequently flow into the third portion of assembly, which houses a collection chamber or collection bag. In the collection chamber or collection bag, the dried plasma is isolated from the humid drying gas and collected using a filter in the collection chamber or bag. For example, the filter in an embodiment is open on one side to receive the flow of humid air and dried plasma and closed on the remaining sides except for an exhaust port. The humid drying gas passes through the filter and is exhausted from the spray drier assembly through an exhaust port in the collection bag.

In some embodiments, the filter is adapted to separate the collection chamber into two parts. The first part of the collection chamber is contiguous with the drying chamber and receives the flow of humid drying gas and dried plasma. The dried plasma is collected in this first part of the collection chamber, while the humid air passes through the filter and is exhausted from the spray drier assembly via an exhaust port in fluid or vapor communication with the second part of the spray drier assembly.

After collecting the dried plasma in the collection chamber or bag, the collection chamber or bag is separated from the spray drier assembly and hermetically sealed. In this manner, the sealed collection chamber or bag is used to store the dried plasma until use. The collection chamber or bag includes a plurality of ports for injection allowing addition of a rehydration solution (e.g., water, buffer) to the collection chamber for reconstitution of the blood plasma and removal of the reconstituted blood plasma for use. The collection chamber or bag may be further attached to a sealed vessel containing rehydration fluid for reconstitution or the container of rehydration fluid may be separate. The collection bag may further comprise an internal filter bag and an external bag for containing the filter bag, wherein both the filter bag and the external bag are vapor permeable or have vapor permeable sections.

Before and after the collection bag the flow path necks down to form segments that are automatically sealed and cut by the instrument to separate the collection bag from the remainder of the disposable for product storage. Alternatively, the collection bag may be sealed and cut manually.

The final section of the disposable ends in a docking port similar to the one at the beginning of the disposable. Once the drying process is completed these ports are automatically re-capped by the instrument and the associated disposable sections are discarded. Only the collection bag is retained for product storage Reference will now be made to FIG. 1, which schematically illustrates one embodiment of a spray drier system 100. The system 100 includes a spray drier device 102 configured to receive a spray drier assembly 104. A source of plasma 112, a source of aerosolizing gas 114, and a source of drying gas 116 are further in fluid or vapor communication with the spray drier assembly 104. During spray drying operations, a flow of the drying gas 116A is caused to flow within the body of the assembly 104 by positive or negative pressure. Concurrently, a flow of a blood plasma 112A and a flow of aerosolizing gas 114A are each caused to flow (either by positive or negative pressure) at selected, respective rates, to a spray drying head 104A of the assembly 104. In the spray drier assembly 104, the flow of blood plasma 112A is aerosolized in the spray drier head 104A and dried in a drying chamber 104B, producing a dried plasma that is collected and stored for future use in a collection chamber or bag 104C. Humid drying gas 122, including condensed moisture (e.g., waste water) removed from the blood plasma during the drying process is further collected for appropriate disposal via the exhaust port of the collection bag.

The spray drier device 102 further includes a spray drier computing device 124, e.g., such as a computer programmed to regulate the spray drying process with minimal operator input. The spray drier computing device 124 is adapted to monitor and control a plurality of process parameters of the spray drying operation. The spray drier computing device 124 further includes a plurality of user interfaces. The spray drier computing device 124 may further communicate with a remote computing device 150 such as a computer programmed to regulate the drying process and record drying data.

Figure 2A:
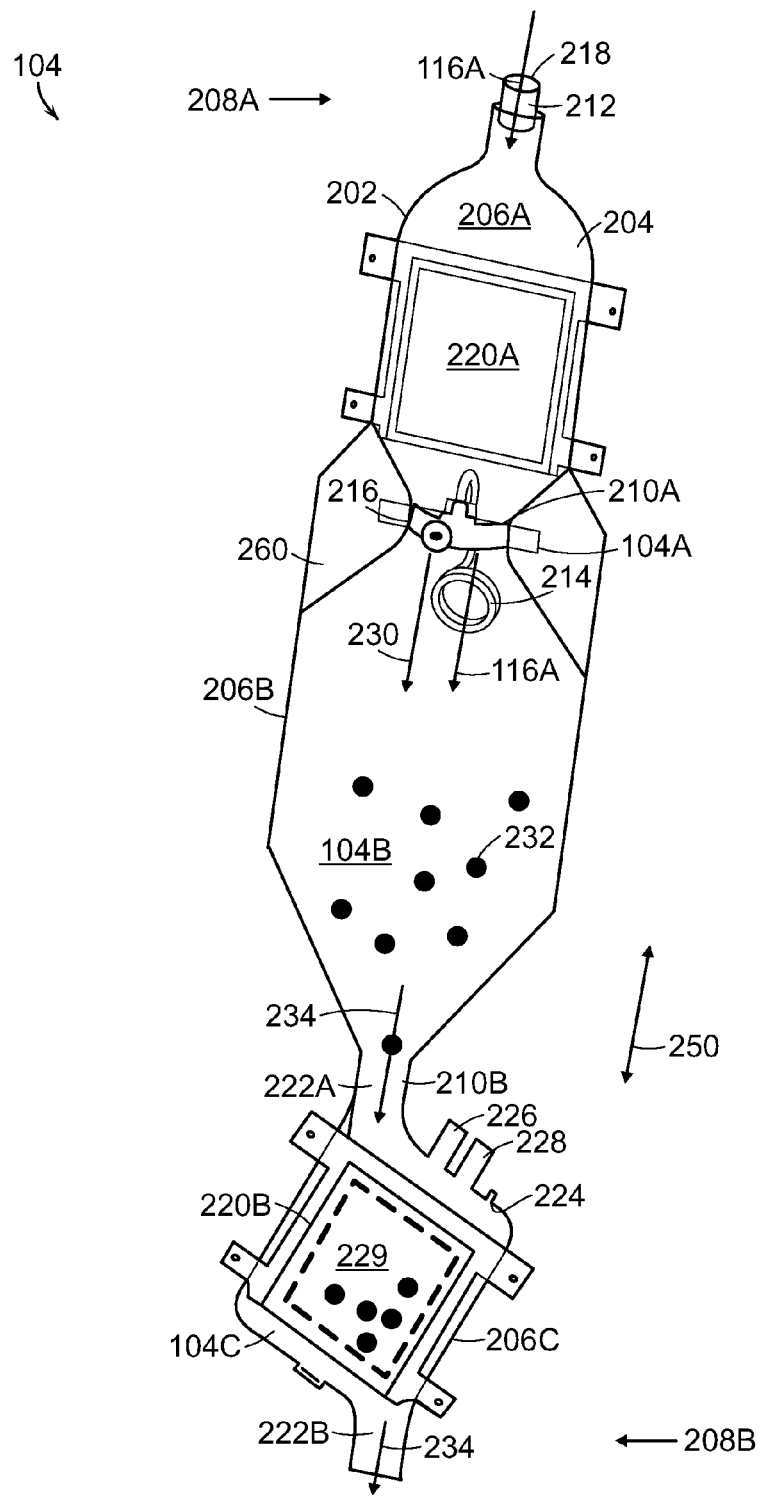
FIGS. 2A and 2B are schematic illustrations of a spray drier assembly according to some embodiments.
Figure 2B:
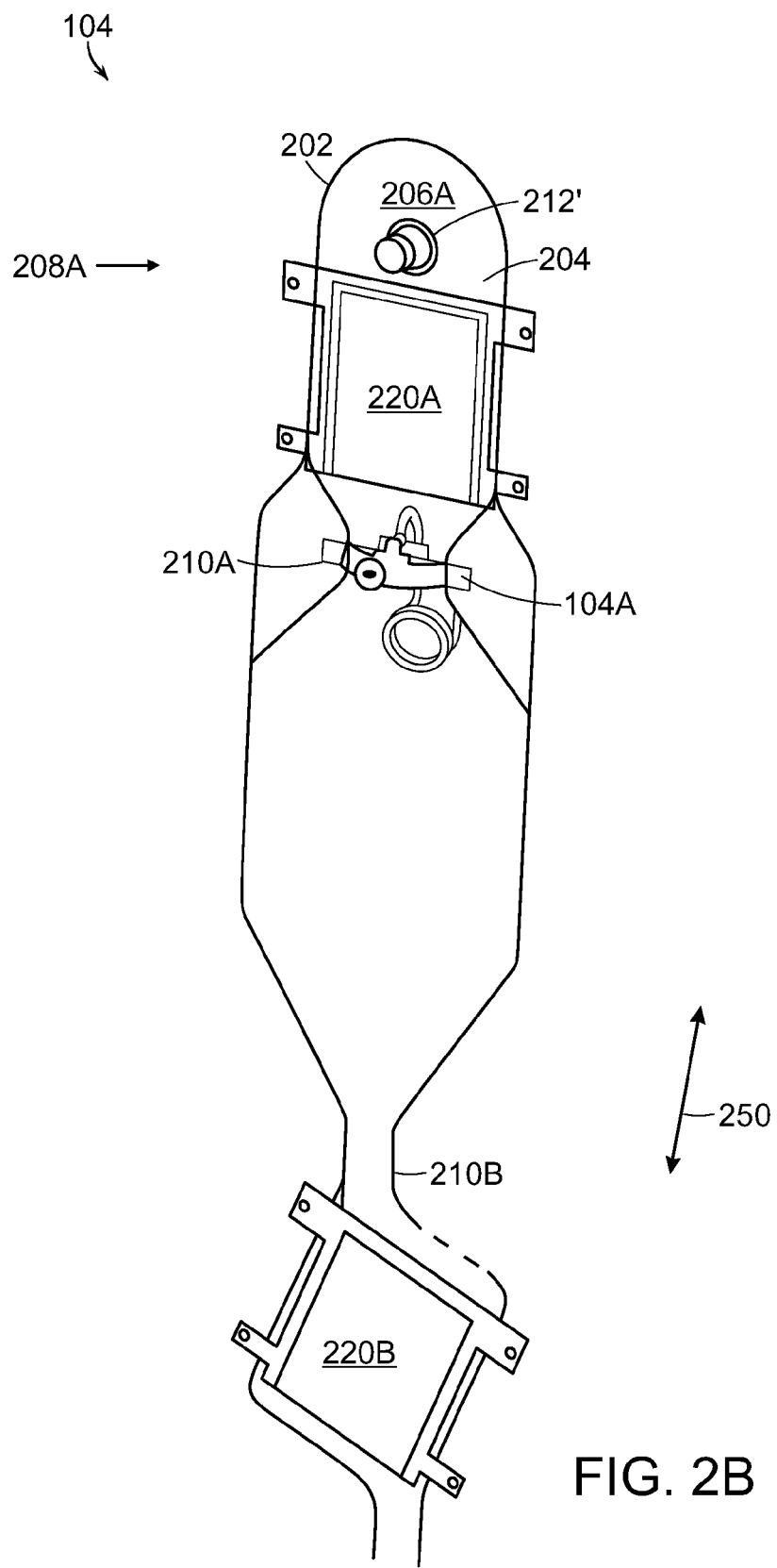

FIGS. 2A and 2B illustrate embodiments of the spray drier assembly 104 in greater detail. As illustrated in FIG. 2A, the spray drier assembly 104 includes a frame 202. An enclosure or body 204 having first and second ends 208A, 208B further extends about and encloses the frame 202. Thus, the body 204 adopts or approximately adopts the shape of the frame 202. The enclosure 204 may further include a dual layer of film sealed together about the periphery of the frame 202.

In some embodiments, the frame 202 may define a first portion 206A, a second portion 206B, and a third portion 206C of the assembly 104. The first portion of the assembly, i.e., portion 206A is positioned adjacent the first end 208A of the body 204. The third portion of the assembly, i.e., portion 206C is positioned adjacent to the second end 208B of the enclosure 204. The second portion of the assembly, i.e., portion 206B is interposed between the first and third portions of the assembly, i.e., portions 206A and 206C.

The frame 202 further defines first and second transition zones 210A, 210B between the first, second, and third portions of the assembly 206A, 206B, 206C. For example, the first transition zone 210A may be positioned between the first and second portions of the assembly 206A, 206B and the second transition zone 210B may be positioned between the second and third portions of the assembly 206B, 206C. In some embodiments, the frame 202 may narrow in width within the transition zones 210A, or 210B, as compared to the width of the surrounding assembly. The relatively narrow transition zones 210A, 210B help to direct the flow of drying gas 116A through the assembly 104.

In further embodiments, the body 204 may include a drying gas inlet 212, adjacent to the first end 208A. The drying gas inlet 212 may be adapted to couple with the spray drier device 102 to form a hermetic and sterile connection that allows the flow of drying gas 116A to enter the assembly 104. In one embodiment, illustrated in FIG. 2A, the drying gas inlet 212 is positioned within the first portion of the assembly 206A, at about the terminus of the first end of the body 208A. In this configuration, the flow of drying gas 116A is received within the assembly 104 in a direction approximately parallel to a long axis 250 of the assembly 104.

In an embodiment of the spray drier assembly 104, illustrated in FIG. 2B, the body 204 may include a drying gas inlet 212'. The position of the drying gas inlet 212' is moved with respect to drying gas inlet 212. For example, the drying gas inlet 212' may be positioned within the first portion of the assembly 206A and spaced a selected distance from the terminus of the first end of the enclosure 208A. In this configuration, the flow of drying gas 116A may be received within the assembly 104 in a direction that is not parallel to the long axis 250 of the assembly 104. For example, in a non-limiting embodiment, the flow of drying gas 116A is received within the assembly 104 in a direction that is approximately perpendicular to the long axis 250 of the assembly 104.

In some embodiments, the spray drier assembly 104 may further include a removable cover 218. The cover 218 may be employed prior to coupling of the spray drier assembly 104 with the spray drier device 102 in order to inhibit contaminants from entering the spray drier assembly. In some embodiments, the cover 218 may be removed immediately prior to coupling with the spray drier device 102 or frangible and penetrated by the spray drier device 102 during coupling with the spray drier assembly 104.

The drying gas 116A received by the assembly 104 is caused to travel from the first portion 206A, through the second portion 206B, to the third portion 206C, where it is removed from the assembly 104. As the drying gas 116A travels within the first portion of the assembly 206A towards the second portion of the assembly 206B, the drying gas 116A passes through a first filter 220A which filters the drying gas 116A entering the assembly 104 in addition to filtering taking place within the spray drier device 102 between the drying gas source 116 and the drying gas inlet 212. In some embodiments, the first filter 220A is a 0.2 micron filter having a minimum BFE (bacterial filtration efficiency) of 106. The filter 220A further helps to ensure the cleanliness of the flow of drying gas 116A.

This process of drying the plasma as it travels through the spray drier assembly 104 may be referred to herein as primary drying. Secondary drying, which further removes moisture from the dried plasma 232 collected within the collection chamber 104C, is discussed in greater detail below. In another embodiment, the flow of aerosolizing gas 114A or drying gas 116A used during primary or (if so used) secondary drying can be supplied by a plurality of heating devices in thermal communication with the spray drier assembly 104. Examples of the heating devices may include, but are not limited to, devices that employ energy such as electromagnetic, radiofrequency, radiation, and microwaves for heating. In this manner, the plurality of heating devices may emit electro-magnetic radiation that passes through the walls of the drying chamber 104B, the collection chamber 104C, or both for heating the flows of aerosolizing gas 114A and/or drying gas 116A therein.

In an embodiment, during primary drying, the flow of drying gas 116A received by the spray drier assembly 104 may possess a temperature from about 50° C. to about 150° C. and a flow rate of from about 15 CFM to about 35 CFM. The flow of aerosolizing gas 116A can possess a flow rate of from about 5 L/min to about 20 L/min and a temperature from about 15° C. to about 30° C. (e.g., 24° C.). The flow of liquid sample 112A may possess a flow rate of from about 3 ml/min to about 20 ml/min. As the plasma is dried, the flow of the aerosolizing gas 114A, the flow of drying gas 116A, or both may direct the flow of the dried sample 232 through at least a portion of the spray drier assembly 104 (e.g., the drying chamber, the collection chamber, or both).

In an embodiment, the assembly 104 may further include a spray drying head 104A, a drying chamber 104B, and a collection chamber or bag 104C in fluid or vapor communication with one another. The spray drying head 104A may be mounted to the frame 202 and positioned within the first transition zone 210A. So positioned, the spray drying head 104A is also positioned within the flow of drying gas 116A traveling from the first portion of the assembly 206A to the second portion of the assembly 206B. The spray drying head 104A may be further adapted to receive the flow of plasma 112A and the flow of aerosolizing gas 114A through respective feed lines 214, 216 and output aerosolized plasma 230 to the drying chamber 104B.

In further embodiments, the drying chamber 104B and collection chamber or bag 104C may be positioned within the second and third portions of the assembly 206B, 206C, respectively. The drying chamber 104B may inflate under the pressure of the flow of drying gas 116A and provides space for the aerosolized blood plasma 230 and the flow of drying gas 116A to contact one another. Within the drying chamber 104B, moisture is transferred from the aerosolized blood plasma 230 to the drying gas 116A (i.e., primary drying), where the drying gas 116A becomes humid drying gas 234. The aerosolized flow of blood plasma 230 and the flow of drying gas 116A are further separated, within the drying chamber 104B, into dried plasma 232 and humid drying gas 234. In some embodiments, the dried plasma 232 may include dried plasma particles that have diameters of less than or equal to 25 μm.

The humid drying gas 234 and dried plasma 232 further proceed into the collection chamber 104C through an inlet port 222A of the collection chamber or bag 104C, positioned within the second transition zone 210B, connecting the collection chamber or bag 104C and the drying chamber 104B. The collection chamber 104 includes a second filter 220B which allows through-passage of the humid drying gas 234 and inhibits through-passage of the dried plasma 232. As a result, the humid drying gas 234 passing through the filter 220B is separated from the dried plasma 232 and exhausted from the collection bag 104C through an exhaust port 222B of the collection bag 104C that forms the second end 208B of the body 204. For example, a vacuum source (e.g., a vacuum pump) may be in fluid or vapor communication with the exhaust port 222B of the collection chamber 104C to force the humid drying gas 234 through exhaust port 222B. Concurrently, the dried plasma 232 is retained in a reservoir 229 of the collection chamber or bag 104C. The collection chamber 104C is subsequently hermetically sealed at about the inlet and exhaust ports 222A, 222B, and detached (e.g., cut) from the spray drier assembly 104, allowing the collection chamber 104C to subsequently function as a storage vessel for the dried plasma 232 until use.

Figure 3:
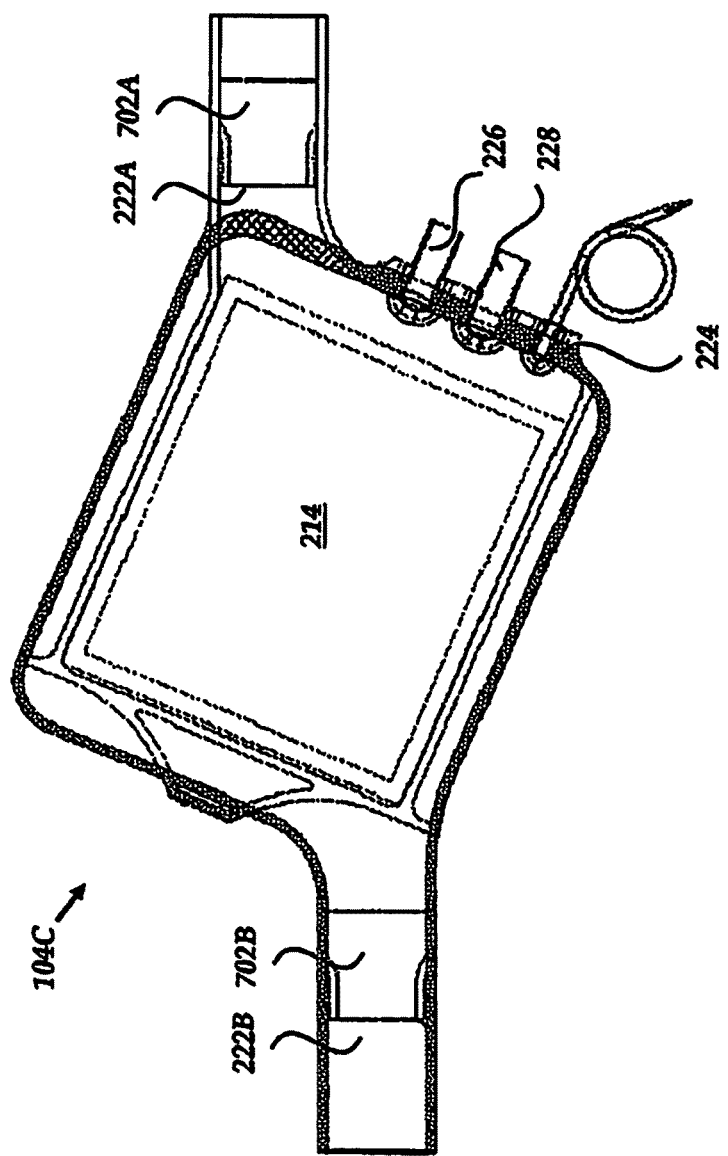
FIG. 3 is a schematic illustration of collection chambers or bags according to some embodiments.

As shown in FIG. 3, the collection chamber 104C may be further configured for use in rehydrating the dried plasma 232. For example, the collection chamber 104C may include a rehydration port 224, a plurality of spike ports 226, and a vent port 228. The rehydration port 224 may be used to communicate with a source of rehydration solution, allowing the rehydration solution to come in contact with the dried plasma 232 within the collection chamber 104C to form reconstituted plasma. The reconstituted plasma may be subsequently drawn from the collection chamber 104C through the spike ports 226.

Exhaust port 222B may be adapted to allow venting of the flow of humid drying gas 234 during secondary drying. For example, in some embodiments, during primary drying, the vents 702A, 702B may allow for gas flow as discussed above and the exhaust port 222B may be closed. During secondary drying, after primary drying is completed, the vents 702A, 702B may be sealed and the exhaust port 222B opened. The exhaust port 222B may be further placed in fluid or vapor communication with a vacuum source (e.g., a vacuum pump) for secondary drying. In further embodiments, a filter (e.g., 0.22 μm or better) may be in line with the exhaust port 222B.

Figure 4A:
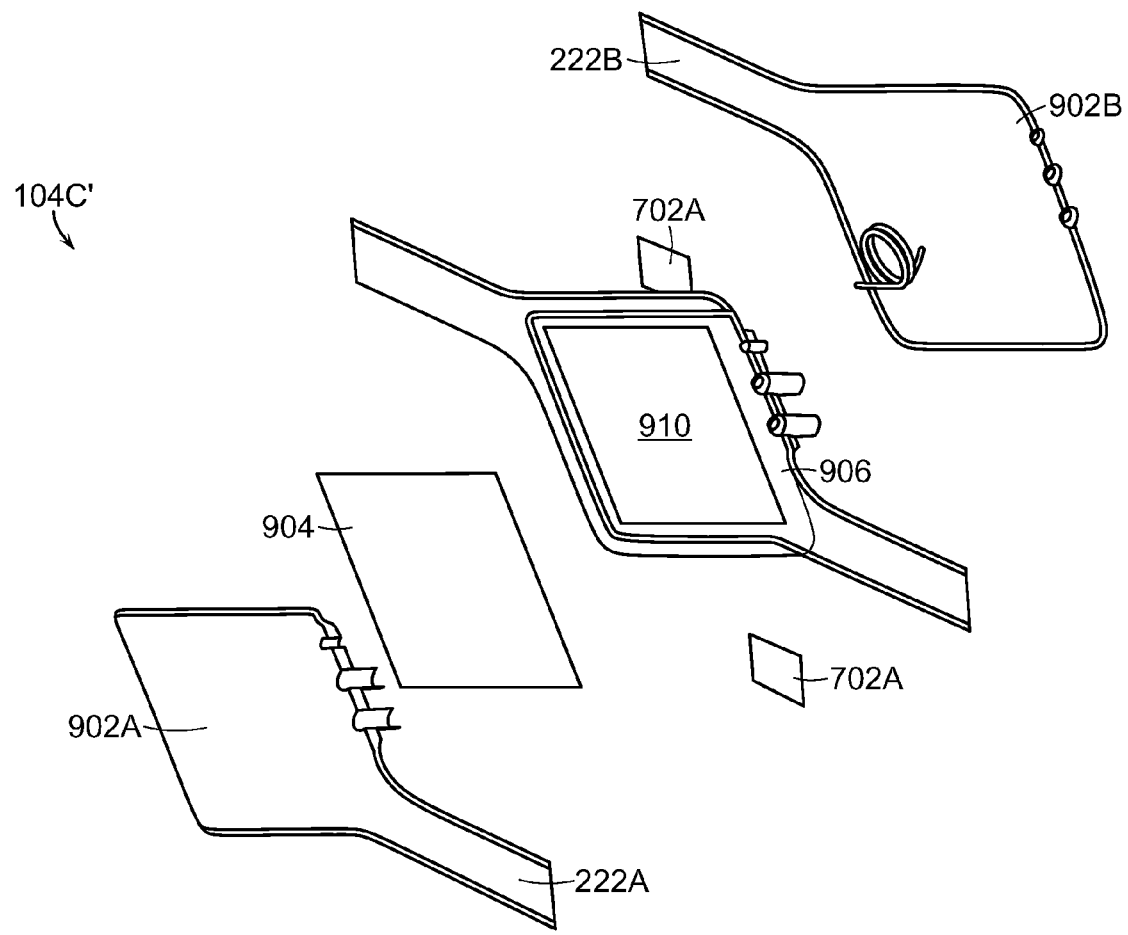
FIGS. 4A-4B are schematic illustrations of collection chambers or bags according to some embodiments.
Figure 4B:
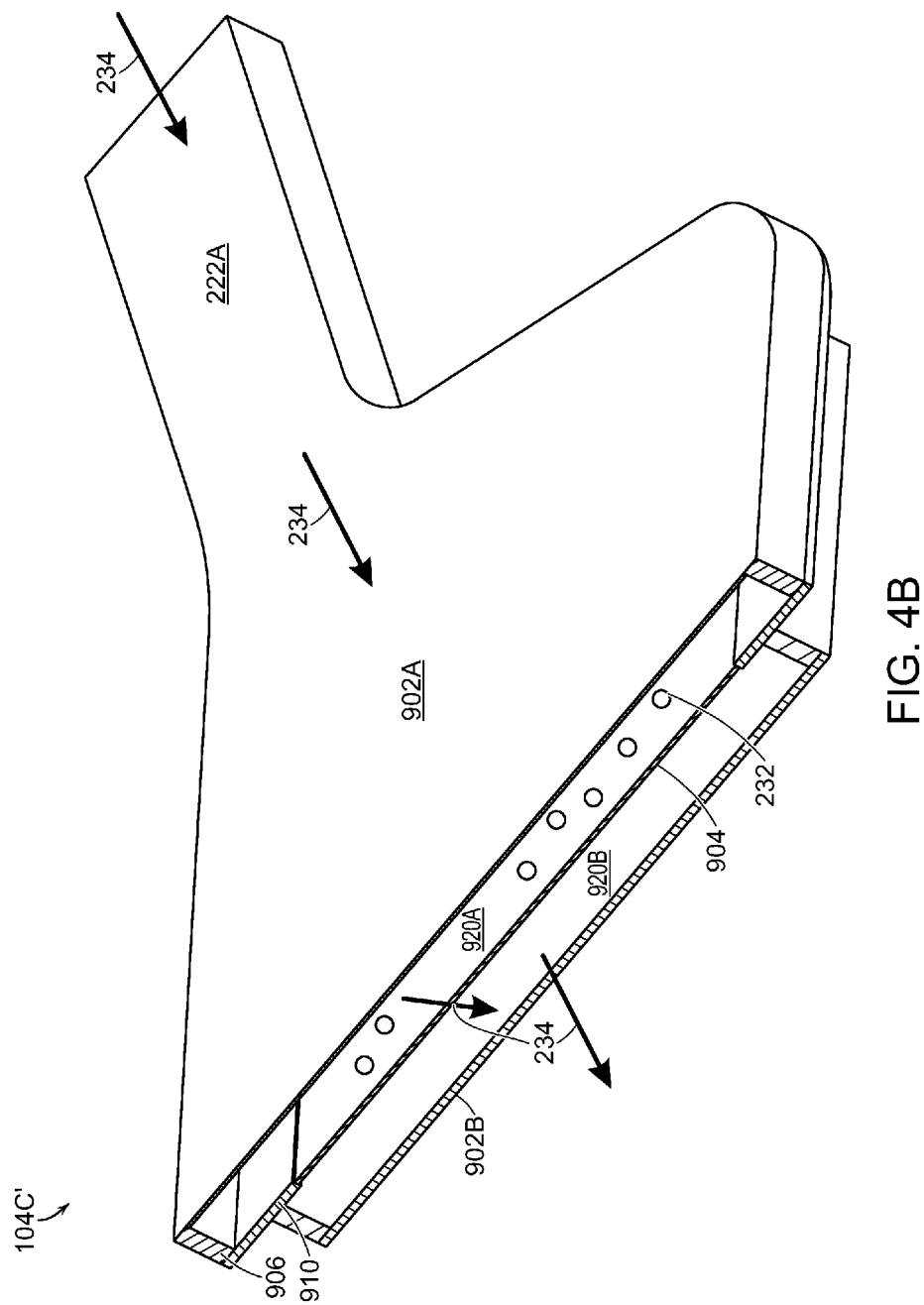

The collection chamber 104C' (see, FIG. 4A for an exploded view of the collection chamber) so constructed is illustrated in cross-section in FIG. 4B. It may be observed that the filter member 904 separates the area enclosed by the collection chamber or bag walls 902A, 902B into two chambers, 920A and 920B. The chamber or bag surround is shown as 906. The filter support is shown as 910. The inlet port 222A of the collection chamber 104C' is in fluid or vapor communication with the chamber 920A. The flow of dried plasma particles 232 and humid drying gas 234 entering the collection chamber 104C' flow into the first chamber 920A. Filter member 904 inhibits the dried plasma particles 232 from passing through the first chamber 920A and into the second chamber 920B, while the humid drying gas 234 freely passes through the filter 904 into the second chamber 920B. Accordingly, the dried plasma particles 232 are retained for storage within the first chamber 920A, while the humid drying gas 234 exits the collection chamber 104C' via the exhaust port 222B.

Spray dried plasma produced using the spray drying apparatus as described above is preferably dried to a first moisture level of 3.5% to 9.5% (but may be another level, which may be determined empirically). This moisture level is referred to herein as the "first moisture level" and is characterized by a substantially "non-clumping" spray dried plasma product. The non-clumping product tends to flow freely into the collection bag, as opposed to clumping, sticking and accumulating within the drying chamber or at points prior to entry into the collection bag or sticking to the processing equipment walls or failing to flow to the collection chamber. Hence, the first moisture level is selected for minimum denaturing and adequate flow properties. Drying to the first moisture level of 3.5% to 9.5% has been determined to optimize recovery of dried blood plasma components such as clotting factors while achieving adequate flow properties. A preferred method for determining moisture levels is described in the Exemplification section, below.

Levels of heat and gas flow during the primary spray drying process (primary drying) contribute to denaturation of blood plasma components. Generally, a higher moisture content of the dried material following the primary spray drying cycle correlates with lower blood plasma component denaturation as a result of using a lower drying temperature. Primary spray drying parameters are controlled to minimize denaturation while attaining good, non-clumping flow properties of the spray dried product. However, moisture at the first moisture level can affect long term storage (i.e., preservation, stability) of the plasma proteins.

While dried plasma prepared through primary spray drying to yield a product having the first moisture level of 3.5% to 9.5% is optimal for recovery of blood plasma components such as clotting factors, a secondary drying process has been determined to substantially improve storage of the product by increasing preservation of the blood plasma proteins. In particular, moisture draw down over time without the use of heat, for example, through exposure to desiccant, has been found to greatly increase the preservation of the plasma proteins. Secondary drying from the first moisture level to a second moisture level of about 1.5% to about 6.0% is discussed in greater detail below.

Next discussed are some embodiments of the collection chamber or bag. The terms are used interchangeably herein. The collection bag comes after the drying chamber. The dried plasma particles arrive at the collection bag entrained in the drying gas air stream. The collection bag filter stops the plasma particles while allowing the drying gas to pass through the filter toward the exhaust port.

The collection bag is constructed with the flow path defined by the outer films with a filter located within the drying bag. The collection bag includes tube ports that are used to introduce the rehydration solution and connect the rehydrated plasma to an infusion set for administration to the patient. These ports are welded between the two films of the bag using a standard tube welding process.

Exemplary material information for the collection bag and storage pouch are as follows:
  Outer collection bag—PVC—American Renolit flexible PVC film (American Renolit, Swedesboro, N.J.), 0.015" thick, DEHP Free, or equivalent. The PVC used is vapor permeable.
  Filter Frame—PVC—American Renolit flexible PVC film, 0.020" or 0.01520" thick, DEHP Free (other thickness can work also), or equivalent.
  Filter Material (Filter Pouch)—Part no. 70P02A-PET—Lydall, UHMW PE w/PET backer 0.2 micron (Lydall, Manchester Conn.), or equivalent.

An example of a suitable storage pouch is the ULINE 10×12" Dri-Shield Moisture Barrier Bag (Part number S-6498), or equivalent One of skill in the art will realize that other suitable materials can be substituted those described above. For example, other vapor permeable materials can be used for the outer collection bag. Further, non-vapor permeable materials can be used if at least a section of the outer collection bag is vapor permeable. Finally, if the spray dried plasma produced through first stage spray drying is to be transferred to a distinct vapor permeable container prior to secondary drying, it is not essential that the collection be vapor permeable.

Figure 5A:
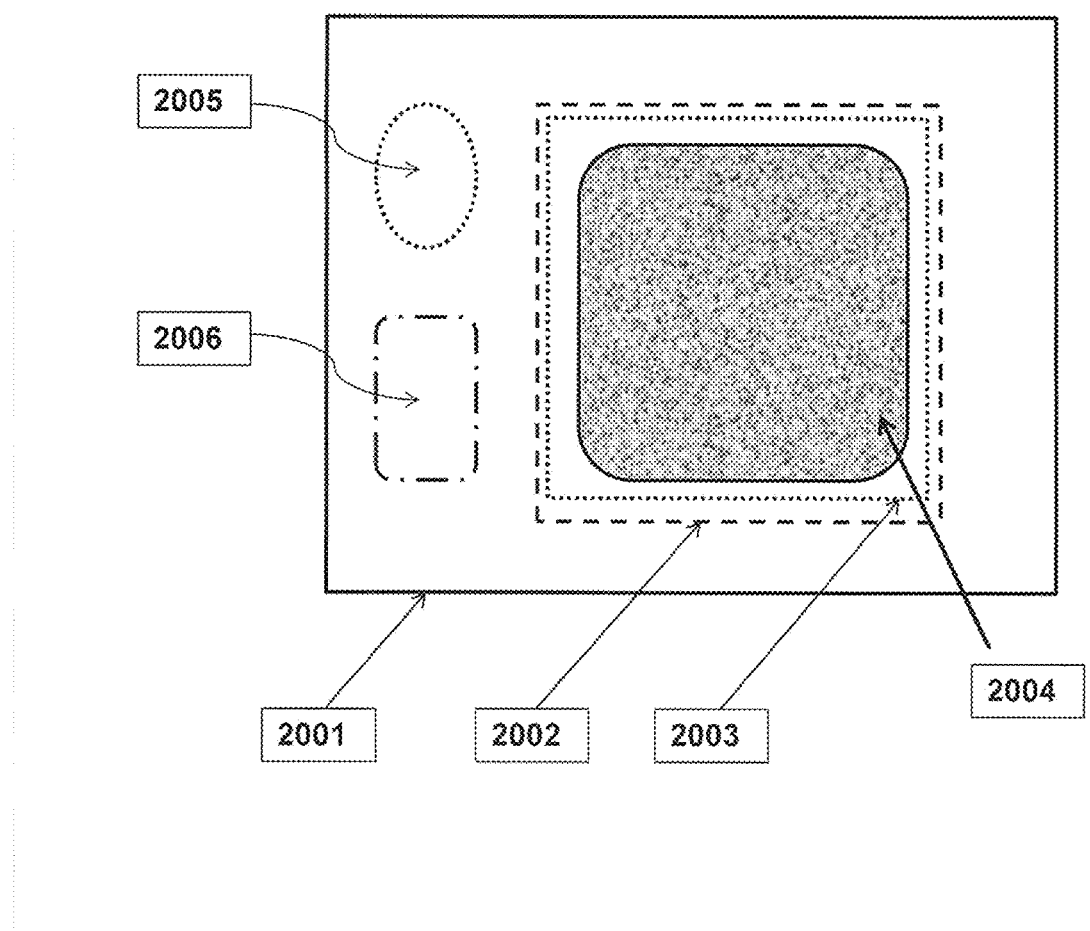
FIGS. 5A-5B are schematic illustrations of the storage pouch containing the collection bag, the desiccant and the oxygen scavenger.
Figure 5B:
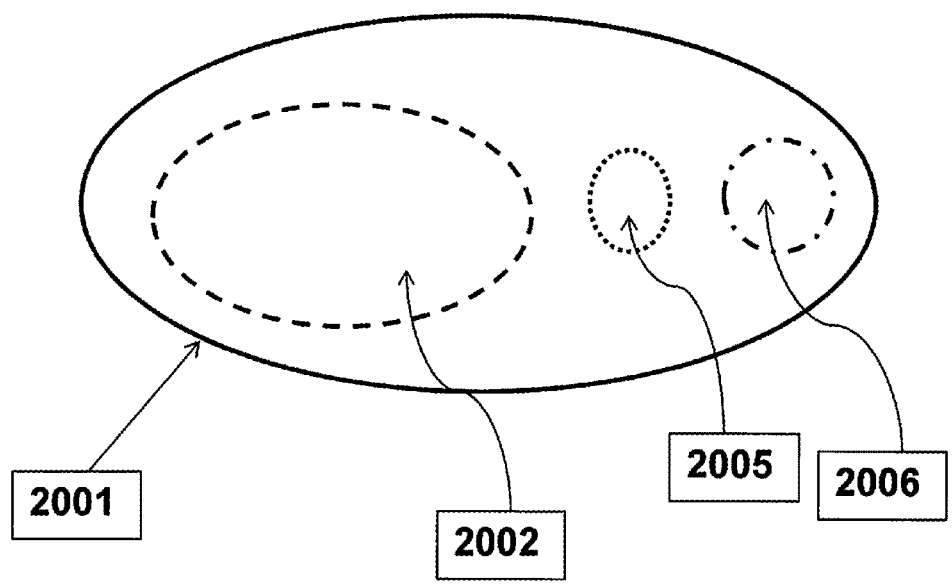

FIGS. 3 and 4A-4B show an embodiment of the collection bag. Further embodiments of the collection bag of the present invention are shown in FIG. 5 (A & B) (porting omitted). FIG. 5A shows a view of a horizontal cross section of a collection bag 2002 within a storage pouch 2001. The collection bag comprises a vapor-permeable filter material 2003 which captures spray dried plasma but allows process air to pass through and out of the spray drier system. The collection bag may have a portion of the surface that is vapor-permeable or the complete surface may be vapor-permeable. The desiccant is preferably held in a container (e.g., canister, sachet or pouch). The desiccant container is located outside the collection bag 2002 and within the storage pouch 2001. Likewise and optionally, the oxygen scavenger is contained in a container outside the collection bag and within the storage pouch. FIG. 5B shows a vertical cross section of the collection bag 2002, desiccant 2005 and oxygen scavenger 2006, located in the storage pouch 2001. Other features of the storage pouch and collection bag described elsewhere in this specification are not shown here merely to not clutter the figure.

The collection bag discussed above is, in preferred embodiments, produced from a plastic film. In the exemplification section that follows, it is demonstrated that a dried blood plasma collection bag produced from PVC, when sealed within a substantially vapor impermeable storage pouch together with a desiccant volume within the storage pouch but external to the collection bag, permits the transfer of moisture in the form of vapor through the walls of the collection bag to the desiccant sink. This process is the secondary drying process.

The gentle withdrawal of moisture from the dried plasma product in this way has been found to decrease the first moisture level to a second moisture level of about 1.5% to 6.0% with little or no further denaturing of the plasma proteins (e.g., clotting factors).

It will be recognized that there is overlap in moisture percentage values specified for the first moisture level and the second moisture level. A bright, non-overlapping line cannot be drawn between these two moisture levels, which are distinguished herein by the process used to achieve them. For example, one skilled in the art will recognize that from run to run in a primary spray dry system, moisture level variations will be observed. Thus, the starting point with regard to the first moisture level produced by the primary spray dry process may be higher in some collection bags as compared to others. In this regard, the secondary moisture level achieved by the secondary drying process with the desiccant will also have variation with higher secondary moisture levels the result of having higher first moisture levels. Therefore, is rare instances, the secondary moisture level may be higher in some collection bags as compared to the first moisture level in other collection bags.

Describing the secondary drying process with greater particularity, dried plasma product which has undergone a primary spray drying cycle is removed from the spray drying apparatus in a sealed, vapor permeable collection bag. Preferably the sealing process is conducted within the spray drying apparatus, but sealing of the collection bag can take place following removal of the collection bag from the spray drying apparatus. In another embodiment the dried plasma product having a first moisture level is removed from the spray dryer and sealed in one of more vapor permeable containers which are then sealed and put in vapor communication with a desiccant material located outside the vapor permeable container, the desiccant material having sufficient capacity to lower the moisture content of the dried plasma product from the first moisture level to a second moisture level. Thus, the dried plasma with a first moisture level may be in the collection bag or chamber or may be removed to another suitable vapor permeable container. The filter bags discussed in the exemplification section, below, are one example of a vapor permeable container that is not a collection bag or collection chamber. Thus, discussion in this specification with regard to obtaining a second moisture level in a collection bag and collection chamber also refer to obtaining a second moisture level in the vapor permeable container described above. Any discussion in the present patent application related to secondary drying of spray dried plasma in a sealed collection bag is equally applicable to the secondary drying of spray dried plasma in a vapor permeable container generally.

The sealed collection bag has at least a vapor permeable section and may be completely or nearly completely vapor permeable. The sealed collection bag is placed or deposited into a storage pouch. The storage pouch is essentially or substantially vapor impermeable. Aluminum lined polymer bags are an example of a suitable storage pouch and are discussed in further detail below. The desiccant is also placed or deposited within the storage pouch external to the collection bag. The desiccant is preferably packaged in vapor permeable containers, pouches or satchels.

Storage pouches house the collection bag and comprise, internal to the storage pouch and external to the collection bag (i.e., between the inner wall of the storage pouch and the outer wall of the collection bag) one or more desiccants and, optionally, one or more oxygen scavengers. The external storage pouches are moisture impermeable or essentially moisture impermeable (i.e., have a very low or moisture transmission rate) and are oxygen impermeable or essentially oxygen impermeable (i.e., have a very low oxygen transmission rate). The storage pouches of the present invention preferably have a moisture vapor transmission rate of about 0.035 $g/m^2$/day or below but may range from about 0.060 $g/m^2$/day to 0.001 $g/m^2$/day or below. An example of a suitable storage pouch is the ULINE 10×12" Dri-Shield Moisture Barrier Bag (Part number S-6498). Other suitable storage pouches are known to or can be readily identified by those of skill in the art.

Secondary drying may be accomplished by any the use of an appropriate amount of desiccant placed either in fluid or vapor communication with the dried plasma outside of the collection chamber or bag but within a storage pouch (outer container) enclosing the collection chamber or bag. So configured, the moisture level of the powder material (i.e., plasma) within the collection chamber or bag may be reduced as the moisture is drawn through a permeable wall of the collection chamber or bag to the desiccant.

It has been recognized that high levels of residual moisture in stored, dried plasma (e.g., moisture contents above about 6% to about 10%, as compared to the moisture content of the liquid plasma), reduce the shelf life (i.e., stability) of the dried plasma. As discussed further herein, this range approximates the moisture level of dried blood plasma recovered from a spray drier when optimized for recovery, which is referred to herein as a first moisture level. Storage at this moisture level may result in damage to plasma proteins, rendering the dried plasma unsuitable for later reconstitution and use. In other words, storage at this moisture level may result in decreased preservation of the plasma protein. Additionally, further drying by processing at elevated temperatures may result in damage to one or more plasma proteins, rendering the dried plasma less suitable for later reconstitution and use. Accordingly, embodiments of secondary drying operations discussed herein are designed to complement the primary spray drying processes discussed above, allowing for further reduction in the moisture content of the plasma (i.e., from a first moisture level to a second moisture level) after primary drying is completed, without significantly damaging the plasma proteins. As a result, the dried plasma stored after undergoing primary and secondary drying is preserved with an improved storage or shelf life remaining suitable for later reconstitution and use. Desiccants are used in the secondary drying process to reduce the first moisture level to a secondary moisture level.

Desiccants are hydroscopic substances that are readily available commercially. Desiccants suitable for use in the present invention include, but are not limited to silica gel, activated charcoal, anhydrous calcium sulfate, calcium chloride, and molecular sieves (typically, microporous, aluminosilicate minerals called zeolites).

The amount of desiccant required for the second phase drying can be calculated as follows. For example, low-humidity molecular sieve desiccant, known in the art, can absorb water equivalent to 20% of its original mass before losing efficacy. This means 5 times mass of desiccant is needed compared to the water it might need to absorb. For example, for about 15 g dried plasma powder and conservatively assuming 10% moisture there will be about 1.5 g of water in the plasma powder. Therefore, 5×1.5=7.5 g desiccant minimum to be capable of absorbing the moisture in the powder. It is not required or even desired to adsorb all of the water from the plasma powder. Further, additional water may penetrate the outer moisture barrier bag at a slow rate. These two conditions should balance out with regard to obtaining a desired moisture content of the plasma power after the second phase drying. One of ordinary skill in the art will be able to calculate or empirically determine the required amount of a selected desiccant to use in view of the teachings provided herein. FIGS. 6A and 6B show differences in efficiency of the secondary drying process based on storage temperature. The figures show that lower storage temperatures result in a lower secondary moisture level when the dried plasma at the first moisture level is in vapor communication with the desiccant. One of skill in the art will be able to determine desiccant amounts suitable for obtaining a desired secondary moisture level at various storage temperatures based on the teachings of this specification.

In addition to providing a desiccant, the present invention also contemplates the use of oxygen scavengers to reduce the oxygen level in the collection bag. The oxygen scavenger is packaged in a canister, satchet or the like, and is put inside the storage pouch and outside of the collection bag. Oxygen scavengers are known in the art and are commonly used in the pharmaceutical industry for protecting, for example, pharmaceuticals, nutraceutical and diagnostic products against oxygen degradation and oxidative reactions. Oxygen scavengers can be metal-based or polymer-based. Metal-based scavengers usually contain ferrous carbonate and a metal halide catalyst and typically require moisture to function. One exemplary commercially available oxygen scavenger is produced by Mitsubishi Gas Chemical Co., Inc. (Tokyo, Japan) and is sold under the trade name PharmaKeep®. PharmaKeep® is a polymer-based oxygen scavenger with a high oxygen absorption capacity of 20 mL $O_2$ per gram scavenger.

The present invention also contemplates a kit. The kit of the present invention comprises a vapor permeable collection bag for collecting the dried plasma product, a desiccant material for removing moisture from the spray dried plasma product and a vapor impermeable storage pouch for storing the vapor permeable collection bag and the desiccant material during processing and storage. The kit may also comprise instructions for use and suitable packaging for transport to destination locations.

The term "fluid communication" shall be described herein as meaning that substances (gas, vapor, liquid, solutions, sols, collides, suspensions or particulates, for example) can move or pass freely from one location to another such as from one section of the drying device of the present invention to another. The movement may be unidirectional or bidirectional, depending on the context described herein. The movement may be continuous or intermittent (i.e., intermittent fluid commination). The movement may be facilitated by external forces such as, but not limited to, positive and negative pressure or may be the result of diffusion.

The term "vapor communication" shall be described herein a meaning that vapor, gas and constituents of the vapor or gas (e.g., water molecules) can move or pass from one location to another such as from one section of the drying device of the present invention to another. The movement may be unidirectional or bidirectional, depending on the context described herein. The movement may be continuous or intermittent (i.e., intermittent vapor commination). The movement may be facilitated by external forces such as, but not limited to, positive and negative pressure or may be the result of diffusion.

The term "vapor permeable" shall be described herein as meaning that gases and substances such as gases or substances which are carried or suspended in a gas (such as, but not limited to water vapor) can move across a material. The material through which gases and vapors can traverse is termed "vapor permeable."

The terms "recover," "recoverable," "recoverability," and similar, as used herein in reference to plasma factors, shall refer to the amount of active plasma factor(s) recovered after the drying process of the present invention. The determination of recovered plasma factors is made, preferably, shortly after drying. Since von Willibrand factor (vWF) is the most heat and moisture labile of the plasma factors, the recovery of vWF will be recognized as being indicative of recoverability of the remaining factors. The measurement of vWF activity is known to those of skill in the art. Two common tests are known in the art. The VWF antigen test measures the amount of vWF protein in the reconstituted plasma of the present invention. vWF activity can be measured by, for example, a glycoprotein (GP)Ib binding assay or a collagen binding assay, both of which are known to those or skill in the art.

The terms "preserve," preserved," and similar, as used herein, in reference to plasma factors, shall refer to the retention of activity of the plasma factors, after drying by the process of the present invention, over a period of time. In other words, it refers to the shelf life of the plasma proteins after drying.

The terms "incubation," "incubating," and similar, as used herein, shall refer to two of more items, substances, etc., being in close proximity for a period of time under controlled environmental conditions. For example, in the context of the present invention, desiccant(s) and/or oxygen scavenger(s) are incubated with the dried plasma in the controlled environment of the vapor-impermeable storage pouch. Within the controlled environment of the vapor impermeable storage pouch moisture is free to pass through the vapor permeable collection bag to the desiccant. Because the desiccant is located outside of the collection bag and inside of the storage pouch, the desiccant is physically separated or physically isolated from the dried plasma of the present invention. Said isolation prevents the contamination of the material in the collection bag such as dried plasma by the desiccant or oxygen scavenger.

EXEMPLIFICATION

The experiments presented here show that a second moisture level can be obtained and maintained after spray drying of the plasma by the method of the present invention. The spray dried plasma has a first moisture level. Upon exposure to a physically isolated desiccant via a vapor permeable barrier, as exemplified below, a second moisture level of the dried plasma product is obtained.

In this experiment plasma was spray dried with Velico (Beverly, Mass.) Medical Breadboard II spray drying instrument and mechanical drying chamber/collection filter (vacuum filter) using the following parameters:
Plasma fluid flow rate: 10 mL/minute
Aerosol gas flow rate: 20 L/minute
Drying gas initial temperature: 125° C.
Drying gas flow rate: 550-750 L/min
Drying gas exhaust temperature: 60° C.

Post drying, the dried plasma was removed from filter (~13 grams) and split up into small batches (~4.5 grams) for the week 2, 4, and 8 time points. Each sub batch was stored in a pouch made from Lydall (Rochester, N.H.) 0.2 micron filter material. The pouches were placed in ULINE (Pleasant Prairie, Wis.) 10×12" Dri-Shield Moisture Barrier Bag (Part number: S-6498) with 2 desiccant packs MiniPax 4A Molecular Sieve Desiccant (weight of desiccant: 0.25 oz.; Minisorb Technologies; Buffalo, N.Y.), absorbent; purchased from McMaster-Carr (Robbinsville, N.J.: PN: 1523T76) and the moisture barrier bag was then heat sealed. FIGS. 5A and 5B are schematic representations of the bags used in the examples of this specification. Samples were stored at 4° C. and 25° C. At each time point a sample was removed and tested for moisture.

Figure 6A:
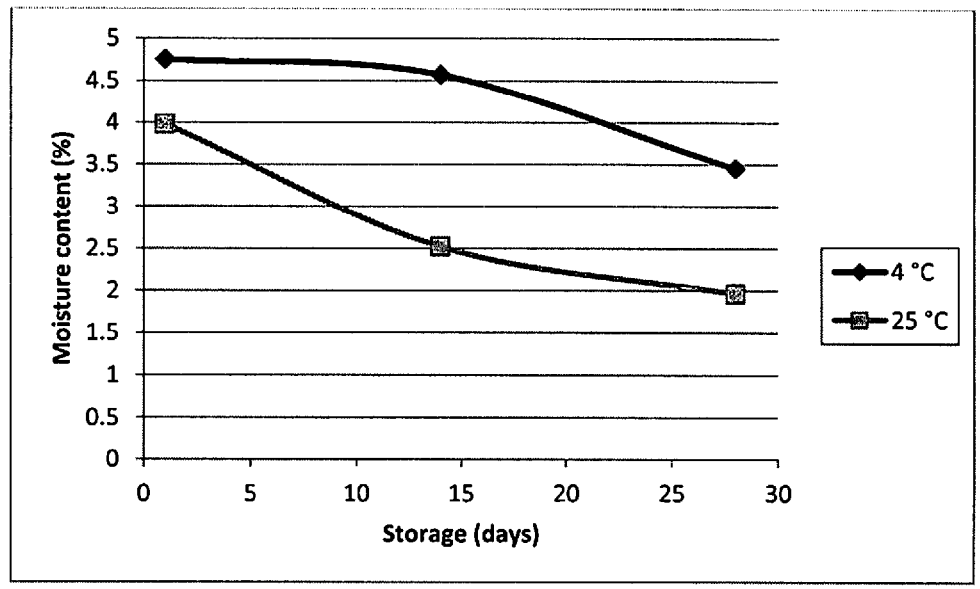
FIGS. 6A-6B are graphs showing the effectiveness of desiccant located between the inner wall of the non-vapor permeable storage pouch and the outer wall of the vapor-permeable collection bag for decreasing the moisture level of the dried plasma of the present invention from a first moisture level to a second moisture level and maintaining the second moisture level.

The moisture content of dried plasma of the present invention in a representative collection bag(s) was determined by the Karl Fischer Titration Method using METTLER TOLEDO KF titrator (Mettler-Toledo AG, Analytical, Schwerzenbach, Switzerland) following the manufacturer's instructions with 0.110-0.200 g of SpDP sample. The collection bag(s) were contained within the storage pouch with a container of desiccant located between the inner wall of the storage pouch and the outer wall of the collection bag. Results are shown in FIGS. 6A & B. First samples were taken on days one, fifteen and twenty-eight after drying. Samples were stored at 4° C. or 25° C. Moisture content of the dried plasma decreased from a first reading of the second moisture level of about 4% to a second moisture level of about 2% over the course of the experiment for the 25° C. storage condition and decreased from a first reading of the second moisture level of about 4.7% to a second moisture level of about 3.5% over the course of the experiment for the 4° C. storage condition. The data points on day one (4.0% & 4.7%) are the initial readings of the second moisture level of the dried plasma product. The experiment shows that the moisture content was maintained at or below this point over the course of the experiment.

Figure 6B:
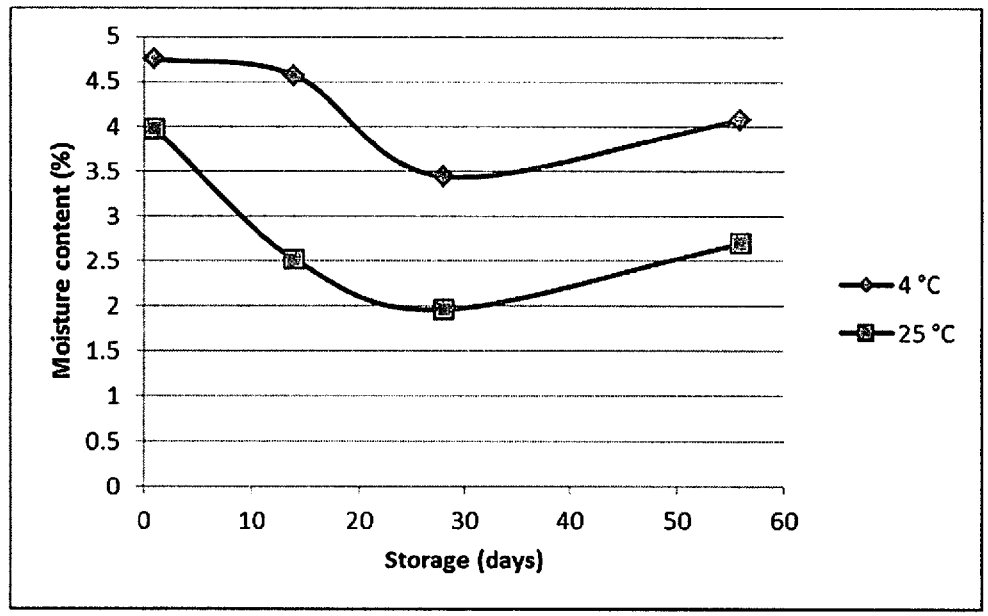
Figure 7:
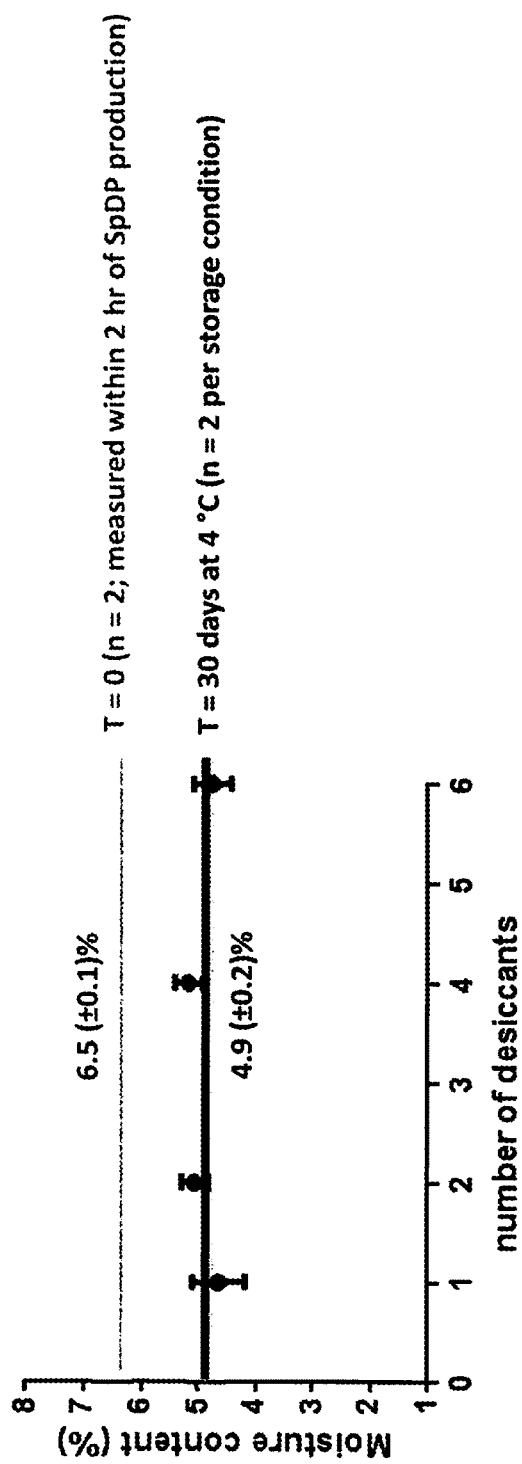
FIG. 7 shows graphs showing the effectiveness of desiccant located between the inner wall of the non-vapor permeable storage pouch and the outer wall of the vapor-permeable collection bag for decreasing a first moisture level to a second moisture level and maintaining a second moisture level.

FIG. 6B shows a similar experiment to the one shown in FIG. 6A using dried plasma of the present invention. For the sample stored at 4° C. samples were taken at days one, fourteen and twenty-eight and additionally at day fifty-eight for the sample stored at 25° C. The results show the moisture content of dried plasma decreased from a first reading of the second moisture level of about 4% at day one to a second moisture level of about 2% at 28 days and 2.6% at 58 days for the 25° C. storage condition. The results show the moisture content of the dried plasma decrease from a first reading of the second moisture level of about 4.6% at day one to a second moisture level of about 3.5% at day 28 before going up to about 4.0% at day 58 for the 4° C. storage condition. The data points on day one (4.7 & 4.0%) are the initial readings of the second moisture level of the dried plasma product. The experiment shows that the moisture content was maintained at or below this point over the course of the experiment. FIGS. 6A & 6B also show how the amount of desiccant used may be determined, at least in part, by storage temperature. This nest experiment shows effectiveness of the second drying step in the method of the present invention. FIG. 7 shows an experiment where the dried plasma product having a first moisture level was stored at 4° C. for 30 days. Plasma was spray dried using Velico Medical Alpha Spray Drying Instrument into collection filter using the following parameters:

Plasma fluid flow rate: 10 mL/minute
Aerosol gas flow rate: 20 L/minute
Drying gas initial temperature: 125° C.
Drying gas flow rate: 550-750 L/min
Drying gas exhaust temperature: 52° C.

Post drying, the inlet and exit port of collection filter bag now filled with dry plasma at a first moisture level were heat sealed. Each bag contained about 15.5 g of dried plasma powder. The sealed vapor permeable collection bag was then placed into a ULINE 10×12" Dri-Shield Moisture Barrier Bag (Part number: S-6498). MiniPax 4A Molecular Sieve (Desiccant, absorbent; weight of desiccant 0.25 oz.) (Purchased from McMaster PN: 1523T76) were also placed in the moisture barrier bag and then the bag was heat sealed. Samples designated for storage were stored in a refrigerator at 4° C. for 30 days. FIG. 7 shows that the initial moisture content (first moisture level) of the dried plasma was about 6.5%±0.1% when measured at 2 ours post drying. Sample bags contained either 1, 2, 4 or 6 desiccant sachets. Sample bags were tested at 30 days. After 30 days the moisture content of the samples bags (second moisture level) averaged 4.9%±0.2% over the 30 day experiment. The experiment shows that 1 or 2 satchels are adequate for obtaining and maintaining a second moisture level of the dried plasma in the collection bag of the present invention.

While several exemplary embodiments and features are described here, modifications, adaptations, and other implementations may be possible, without departing from the spirit and scope of the embodiments. Accordingly, unless explicitly stated otherwise, the descriptions relate to one or more embodiments and should not be construed to limit the embodiments as a whole. This is true regardless of whether or not the disclosure states that a feature is related to "a," "the," "one," "one or more," "some," or "various" embodiments. Instead, the proper scope of the embodiments is defined by the appended claims. Further, stating that a feature may exist indicates that the feature may exist in one or more embodiments.

In this disclosure, the terms "include," "comprise," "contain," and "have," when used after a set or a system, mean an open inclusion and do not exclude addition of other, non-enumerated, members to the set or to the system. Further, unless stated otherwise or deducted otherwise from the context, the conjunction "or" is often used not exclusively, but inclusively to mean or. Moreover, as used in this disclosure, a subset of a set may include one or more than one, including all, members of the set.

The terms about, approximately, substantially, and their equivalents may be understood to include their ordinary and customary meaning. In addition, these terms may be understood to represent values close to a specified value which they modify. For example, within 10% of, within 9% of, within 8% of, within 7% of, within 6% of, within 5% of, within 4% of, within 3% of, within 2% of, within 1% of, within 0.9% of, within 0.8% of, within 0.7% of, within 0.6% of, within 0.5% of, within 0.4% of, within 0.3% of, within 0.2% of, within 0.1% of, etc., of a specified value.

All percents (%) are w/w unless specifically indicated otherwise.

The foregoing description of the embodiments has been presented for purposes of illustration only. It is not exhaustive and does not limit the embodiments to the precise form disclosed. Those skilled in the art will appreciate from the foregoing description that modifications and variations are possible in light of the above teachings or may be acquired from practicing the embodiments. For example, the described steps need not be performed in the same sequence discussed or with the same degree of separation. Likewise various steps may be omitted, repeated, combined, or performed in parallel, as necessary, to achieve the same or similar objectives. Similarly, the systems described need not necessarily include all parts described in the embodiments, and may also include other parts not described in the embodiments. Accordingly, the embodiments are not limited to the above-described details, but instead are defined by the appended claims in light of their full scope of equivalents.

We claim:

1. A method for spray drying blood plasma, the method comprising:
   providing a spray drier device having a collection bag;
   providing blood plasma;
   spray drying the blood plasma using the spray drier device to produce a dried plasma product recovered in the collection bag, said dried plasma product having a moisture content at a first moisture level, wherein the first moisture level is associated with a substantially non-clumping dried plasma;
   removing the collection bag containing the dried plasma product from the spray drier device and sealing the dried plasma product in a vapor permeable container;
   incubating the sealed vapor permeable container containing dried plasma product in vapor communication with a desiccant material stored in a container, located outside the sealed vapor permeable container having sufficient capacity to lower the moisture content of the dried plasma product from the first moisture level to produce a dried plasma product at a second moisture level.

2. The method of claim 1, wherein the vapor permeable container is the collection bag.

3. The method of claim 1, wherein a plasma factor activity in the dried plasma product is determined to retain a greater activity through storage at the second moisture level relative to storage at the first moisture level.

4. The method of claim 1, wherein the first moisture level is from about 3.5% w/w to about 9.5% w/w.

5. The method of claim 1, wherein the second moisture level is from about 1.5% w/w to about 6.0% w/w.

6. The method of claim 1, wherein a mass of desiccant material is provided as a function of a mass of the dried plasma product, the first moisture level, and the second moisture level.

7. The method of claim 1, wherein a mass of desiccant material is provided as a function of storage temperature.

8. The method of claim 1, wherein incubating the dried plasma product further comprises storing both the collection bag and the desiccant material within a sealed, vapor impermeable storage pouch.

9. The method of claim 1, further comprising storing an oxygen scavenger material outside of the collection bag, wherein the dried plasma maintains vapor communication with the oxygen scavenger material through the collection bag.

10. The method of claim 1, wherein said collection bag is sealed prior to being removed from the spray drier device.

11. The method of claim 10, wherein a mass of desiccant material is provided as a function of a mass of the dried plasma product, the first moisture level, and the second moisture level.

12. The method of claim 1, wherein the sealed vapor permeable container containing dried plasma product is in vapor communication with a composition consisting of desiccant material located outside the sealed vapor permeable container.

13. A method for storing dried plasma product, the method comprising:
providing a spray dryer, a vapor-permeable collection bag, a vapor impermeable storage pouch, desiccant and blood plasma drying the blood plasma in the spray dryer to produce a dried plasma product containing preserved blood plasma clotting factors, the dried plasma product having a moisture content at a first moisture level, wherein the first moisture level is associated with a substantially non-clumping dried plasma product, and collecting the dried plasma product in the vapor permeable collection bag;

placing the collection bag containing the dried plasma product in the vapor non-permeable storage pouch containing the desiccant wherein the desiccant is located in a container in the storage pouch outside the collection bag; wherein the desiccant is selected at an amount sufficient to absorb moisture from the dried plasma through the collection bag and to lower the moisture content of the dried plasma product to a desired second moisture level and wherein the desired second moisture level is selected for a combination of stability and preservation of the clotting factors.

14. The method of claim 13, wherein the collection bag comprises:
an internal filter bag for containing the dried plasma product; and
an external bag for containing the filter bag, wherein both the filter bag and the external bag are vapor permeable.

15. The method of claim 14, wherein the external bag comprises polyvinyl chloride (PVC).

16. The method of claim 14, wherein the filter bag comprises 0.2 micron filter material.

17. The method of claim 13, wherein the first moisture level is from about 3.5% w/w to about 9.5% w/w.

18. The method of claim 13, wherein the second moisture level is from about 1.5% w/w to about 6.0% w/w.

19. The method of claim 13, wherein a mass of desiccant is provided as a function of storage temperature.

20. The method of claim 13, wherein the sealed vapor permeable container containing dried plasma product is in vapor communication with a composition consisting of desiccant material located outside the sealed vapor permeable container.

* * * * *